(12) United States Patent
Dolby et al.

(10) Patent No.: US 7,598,394 B2
(45) Date of Patent: Oct. 6, 2009

(54) PROCESS FOR THE SYNTHESIS OF IMIDAZOLES

(75) Inventors: Lloyd J. Dolby, Eugene, OR (US); Shervin Esfandiari, Eugene, OR (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 116 days.

(21) Appl. No.: 11/623,693

(22) Filed: Jan. 16, 2007

(65) Prior Publication Data

US 2007/0185332 A1    Aug. 9, 2007

Related U.S. Application Data

(63) Continuation-in-part of application No. 10/706,474, filed on Nov. 11, 2003, now Pat. No. 7,183,305.

(51) Int. Cl.
C07D 233/66 (2006.01)
A61K 31/4174 (2006.01)

(52) U.S. Cl. .................... 548/335.1; 514/396
(58) Field of Classification Search .............. 548/335.1; 514/396
See application file for complete search history.

(56) References Cited

U.S. PATENT DOCUMENTS

| 4,771,117 | A | * | 9/1988 | Citron et al. ................ 526/194 |
| 5,578,616 | A | | 11/1996 | Asianiam et al. |
| 5,658,903 | A | | 8/1997 | Adams et al. |
| 6,008,240 | A | | 12/1999 | Phillips et al. |
| 6,235,740 | B1 | | 5/2001 | Barrish et al. |
| 6,329,369 | B1 | | 12/2001 | Chow et al. |

FOREIGN PATENT DOCUMENTS

| EP | 0591027 | 4/1994 |
| WO | WO9626927 | 9/1996 |
| WO | WO9629315 | 9/1996 |
| WO | WO9823224 | 6/1998 |
| WO | WO 9924421 | 5/1999 |
| WO | WO9928315 | 6/1999 |
| WO | WO0023438 | 4/2000 |
| WO | WO0109128 | 2/2001 |
| WO | WO-03/099795 | * | 5/2003 |

OTHER PUBLICATIONS

Janzen et al, "N-tert-butyldimethylsilyl)imidazole and related heterocycles: 13C Nuclear magnetic resonance study and reaction with dimethylsulfoxide," Canadian Journal of Chemistry (1980), vol. 58(1), pp. 60-64.*
Overberger et al, "Esterolytic Activity of Imidazole-Containing Polymers. Synthesis and Characterization of Copoly[1-alkyl-4 or 5-Vinylimidazole/4(5)-Vinylimidazole] and its Catalytic Activity in the Hydrolysis of p-Nitropehenyl Acetate," J. Polym. Sci.(1978), vol. 60 (6), pp. 1237-1248.*
Nispen, et al., "Use of dilithio-tosylmethyli isocyanide in the synthesis of oxazoles and imidazoles," Tetrahedron Letters, vol. 21, 1980, pp. 3723-3726.
Ranganathan, et al., "Convenient synthesis of 2-thionaphthylmethyl isocyanide: a useful reagent for methyl isocyandie transfer," vol. 29, No. 12, 1988, pp. 1435-1436.
Sisko, et al., An Investigation of Imidazole and Oxazole Synthesis Using Aryl-substituted Tos MIC Reagents,: J. Org. Chem. 2000, 65, pp. 1515-1524.
Ten Have, et al., "Novel Synthesis of 4(5)-Monosubstituted Imdiazoles vis Cycloaddition of Tosylmethyl Isocyanide to Aldimines," Tetrahedron, 1997, vol. 53, No. 33, pp. 11355-11368.
Van Leusen, et al., "Base-Induced Cycloaddition of Sulfonylmethyl Isocyanides to C, N Double Bonds. Synthesis of 1,5-Disubstituted and 1,4,5-Trisubstituted Imidazoles from Aldimines and Imidoyl Chlorides," J Org. Chem. 1977, 42, 1153.
Horne, et al., "A Two-Step Synthesis of Imidazoles from Aldehydes Via 4-Tosyloxazolines," Heterocycles, 1994, vol. 39, No. 1, pp. 139-153.
S. Marcaccini, "The Use of Isocyanides in Heterocyclic Synthesis. A Review," Organic Preparations and Procedures Int. 1993, 25 (2), pp. 141-208.
N. Shih, "Novel Synthesis of N-Unsubstituted Imidazoles Using N-Trimethylsilylimines," Tetrahydron Letters, 1993, vol. 34, No. 4, pp. 595-598.
Mor, et al., Synthesis and biological assays of new Hc-antagonists with imidazole polar groups,: Il Farmaco, 55, 2000, 27-24.

* cited by examiner

Primary Examiner—Rei-Tsang Shiao
Assistant Examiner—Janet L Coppins
(74) Attorney, Agent, or Firm—Allergan, Inc.; Kevin J. Forrestal

(57) ABSTRACT

The present invention provides a process for the preparation of imidazoles by reacting a cyano compound with a silylalkylisocyanide compound. Such imidazoles are useful pharmacologically-active compounds and/or intermediates for the preparation of pharmacologically-active compounds.

2 Claims, 1 Drawing Sheet

PROCESS FOR THE SYNTHESIS OF IMIDAZOLES

CROSS-REFERENCE TO RELATED APPLICATIONS

Figure 1:
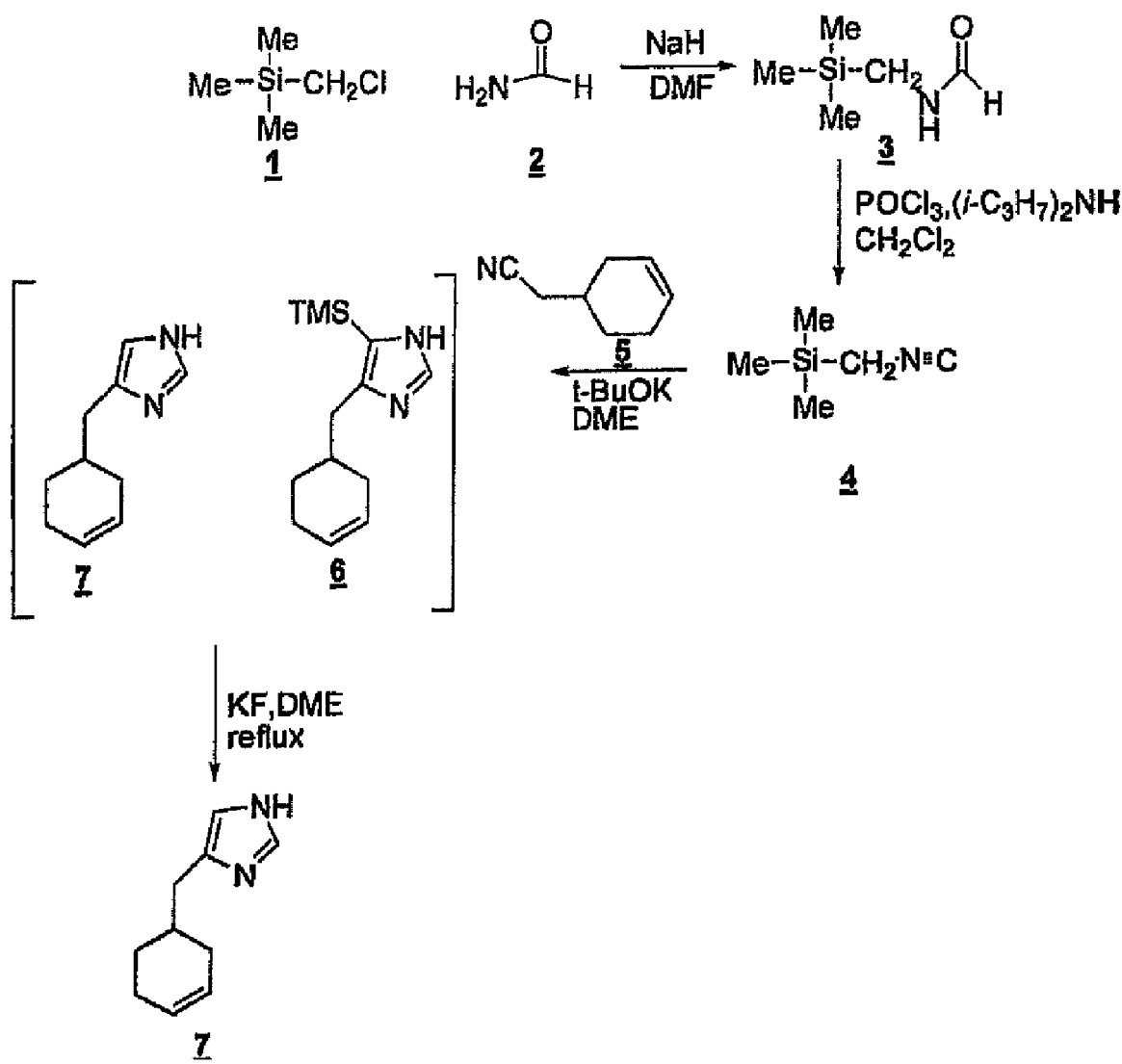

This patent application is a continuation in part of U.S. patent application Ser. No. 10/706,474, filed on Nov. 11, 2003, now U.S. Pat. No. 7,183,305 which is incorporated by reference herein, and claims priority thereto under 35 U.S.C. § 120.

FIELD OF THE INVENTION

The present invention provides a process for the preparation of imidazoles by reacting a cyano compound with a silylalkylisocyanide compound. Such imidazoles are useful pharmacologically-active compounds and/or intermediates for the preparation of pharmacologically-active compounds.

BACKGROUND OF THE ART

Imidazoles are a common component of a large number of natural products and pharmacologically active molecules. The prevalence and importance of this component makes methods which facilitate their preparation highly valuable. Despite intensive synthetic interest in these heterocycles during the past century, few methods have emerged which are general and capable of delivering highly functionalized imidazoles. In addition, many of the available methods utilize intermediates which are difficult to prepare, such as α-functionalized carbonyl and α-diamino compounds. One approach to imidazole synthesis involves cycloaddition of tosylmethyl isocyanides (TosMICs) to carbon-nitrogen double bonds. (See van Leusen et al J. Org. Chem. 1977, 42, 1153.)

The synthesis of imidazoles from TosMIC and imines is reported in Sisko et al.; *J. Org. Chem.* 2000, 65, 1515-24, "An Investigation of Imidazole and Oxazole Synthesis Using Aryl-Substituted TosMIC Reagents".

See also U.S. Pat. No. 5,658,903 to Adams et al.; ten Have et al., *Tetrahedron,* 1997, Vol. 53, No. 33., pp. 11355-11368, "Novel Synthesis of 4(5)-Monosubstituted Imidazoles via Cycloaddition of Tosylmethyl Isocyanide to Aldimines"; Home et. al., *Heterocycles,* 1994, Vol. 39, No. 1, pp. 139-153, "A Two-Step Synthesis of Imidazoles From Aldehydes Via 4-Tosyloxazolines"; S. Marcaccini, *Organic Preparations and Procedures Int.,* 1993, 25 (2), pp. 141-208, "The Use of Isocyanides in Heterocyclic Synthesis. A Review"; and N. Shih, *Tetrahydron Letters,* 1993, Vol. 34, No. 4, pp. 595-598, "Novel Synthesis of N-Unsubstituted Imidazoles Using N-Trimethylsilylimines" for other synthetic methods for preparing imidazoles.

BRIEF SUMMARY OF THE INVENTION

The present invention provides a method for preparing an imidazole compound having the formula

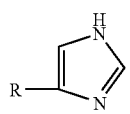

wherein R is selected from the group consisting of aryl, alkyl, alkenyl and alkynyl radicals and substituted derivatives thereof, wherein said substituted derivatives may include one or more heteroatoms selected from the group consisting of halogen, oxygen, nitrogen sulfur and phosphorus atoms, which comprises reacting a cyano compound having the formula R—C≡N, wherein R is not bonded to the cyano group through a S, O or N atom and R does not include a H atom allylic or benzylic to the cyano group, with a silylmethyl isocyanide compound to yield

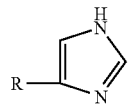

when R is aryl, R may be carbocyclic aryl e.g. phenyl, naphthyl, etc. or heterocyclic aryl, e.g. furyl, thienyl, pyridyl, etc.

DESCRIPTION OF THE DRAWING FIGURE

The FIGURE describes a synthetic scheme illustrating the method of the invention.

DETAILED DESCRIPTION OF THE INVENTION

The following pharmacologically-active imidazole compounds may be prepared by the method of this invention:

Indanylimidazoles, as described in PCT Int. Appl. WO 97 12874 which is hereby incorporated by reference in its entirety.

Imidazole-alkyl carbazole or fluorenyl compounds, as disclosed in PCT Int. Appl. WO 9626927-A1 which is hereby incorporated by reference in its entirety.

Phenyl-alkyl-imidazoles, as disclosed in U.S. Pat. No. 5,578,616 which is hereby incorporated by reference in its entirety.

Imidazoylalkyl compounds substituted with a heterocyclic ring containing one nitrogen atom, as disclosed in PCT Int. Appl. WO 99/24421 and 98/23224 which is hereby incorporated by reference in its entirety.

2-(1H-4(5)-Imidazoyl) cyclopropyl derivatives, as disclosed in U.S. Pat. No. 6,008,240 which is hereby incorporated by reference in its entirety.

Imidazole derivatives, as disclosed in PCT Int. Appl. WO 09928315-A1 which is hereby incorporated by reference in its entirety.

Heterocyclic-substituted imidazole derivatives, as disclosed in PCT Int. Appl. WO 9924421-A1 which is hereby incorporated by reference in its entirety.

Thiourea and isothiourea derivatives, as disclosed in PCT Int. Appl. WO 01/09128 A1 which is hereby incorporated by reference in its entirety.

Imidazole derivatives as disclosed in Mor et al., *Il Farmaco,* 55, 2000, pp. 27-24 which is hereby incorporated by reference in its entirety.

N-(imidazoylalkyl) substituted cyclic amines, as disclosed in PCT Int. Appl. WO 200023438-A1 which is hereby incorporated by reference in its entirety.

Imidazole derivatives, as disclosed in PCT Int. Appl. WO 96/29315 which is hereby incorporated by reference in its entirety.

Piperidinylimidazoles as disclosed in European Patent Application 0 591 027 A1 which is hereby incorporated by reference in its entirety.

Preferably, the method of the present invention may be used to prepare the imidazoles disclosed in U.S. Pat. No. 6,329,369 which is hereby incorporated by reference in its entirety.

The method of the present invention may be practiced in a liquid phase reaction medium, under an inert atmosphere, e.g. Argon, at a temperature between 50 and −100° C., preferably between −20 and 25° C. and more, preferably between −15 and 0° C., e.g. at room temperature. The reaction may be carried out at any operable pressure, e.g. atmospheric pressure. The reaction time may vary from 1 hr. to 6 hrs., preferably from 2 hrs. to 4 hrs.

The reaction product may be separated from the liquid phase reaction medium by methods known in the prior art, e.g. distillation, crystallization, etc.

Thus, a compound having selective agonist activity at the α2B or α2B/2C adrenergic receptor subtype(s) as compared to the 2A adrenergic receptor subtype, as disclosed in U.S. Pat. No. 6,329,369 is prepared by the method of this invention.

These compounds are represented by the general formula

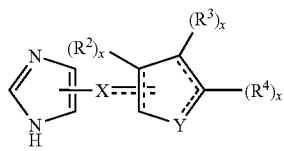

I wherein the dotted lines represent optional bonds provided that two double bonds may not share a common carbon atom; $R^5$ is H or lower alkyl; X is $C(H)R^1$, wherein $R^1$ is H or lower alkyl, but $R^1$ is absent when the bond between X and the ring represented by

is a double bond; Y is O, N, S, $(CR^1{}_2)_y$, wherein y is an integer of from 1 to 3, —CH=CH— or —$Y^1CH_2$—, wherein $Y^1$ is O, N or S; x is an integer of 1 or 2, wherein x is 1 when $R^2$, $R^3$ or $R^4$ is bound to an unsaturated carbon atom and x is 2 when $R^2$, $R^3$ or $R^4$ is bonded to a saturated carbon atom; $R^2$ is H, halogen, hydroxy, lower alkyl, alkoxy, alkenyl, acyl, alkynyl, or, when attached to a saturated carbon atom, $R_2$ may be oxo; $R_3$ and $R_4$ are, each, H, halogen, lower alkyl, alkenyl, acyl, alkynyl, aryl, e.g. phenyl or naphthyl, heteroaryl, e.g. furyl, thienyl, or pyridyl, and substituted aryl or heteroaryl, wherein said substituent may be halogen, lower alkyl, alkoxy, alkenyl, acyl, alkynyl, nitro, cyano, trifluoromethyl, hydroxy, etc. or, together, are —$(C(R^2)x)z$-; —$Y^1(C(R^2)x)z'$-; —$Y^1(C(R^2)x)y$ $Y^1$—; —$(C(R^2)x)$- $Y^1$—$(C(R^2)x)$-; —$(C(R^2)x)$- $Y^1$—$(C(R^2)$ x)-$(C(R^2)x)$- and —$Y^1$—$(C(R^2)x)$- $Y^1$—$(C(R^2)x)$- wherein z is an integer of from 3 to 5, z' is an integer of from 2 to 4 and x and y are as defined above, and further either end of each of these divalent moieties may attach at either R3 or R4 to form a condensed ring structure shown generally as

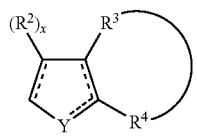

and the rings formed may be totally unsaturated, partially unsaturated, or totally saturated provided that a ring carbon has no more than 4 valences, nitrogen no more than three and O and S have no more than two.

In another aspect of the invention in the above compound is represented by the formula

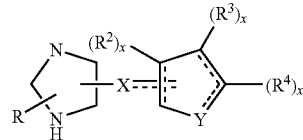

II wherein X may be $C(H)R^1$ and $R^1$ is H.

In said compound of formula II, $R_2$ may be H and

may represent a furanyl radical.

In such furanyl derivatives of Formula II, $R^3$ and $R^4$ together may be $(CH)_4$, or $R^3$ may be H and $R^4$ may be t-butyl, or $R^3$ and $R^4$ may be H, or $R^3$ may be H and $R^4$ may be methyl or ethyl.

Alternatively, in the compound of Formula I, $R^1$ may be methyl and

may represent a furanyl radical.

Alternatively, in said compounds of Formula II, $R^2$ may be H and

may represent a thienyl radical.

In such thienyl derivatives of Formula II, $R^3$ and $R^4$, together, may represent $(CH_2)_4$, or $R^3$ may be phenyl and $R^4$ may be H, or $R^3$ and $R^4$, together, may represent $(CH_2)_3S$, or $R^3$ and $R^4$ may be H, or $R^3$ and $R^4$, together, may represent $(CH)_4$, or may be $R^3$ may be H and $R^4$ may be methyl, or $R^3$ may be bromo and $R^4$ may be H, or $R^3$ may be hydrogen and $R^4$ may be chloro, or $R^3$ may be methyl and $R^4$ may be hydrogen.

Alternatively, in the compounds of Formula II

may represent a cyclohexyl radical.

In such cyclohexyl derivatives of Formula II, $R^2$ may be hydrogen and $R^3$ and $R^4$ may, together, represent $(CH)_4$, or $R^2$ may be oxo and $R^3$ and $R^4$, together, may be $(CH)_4$, or $R^2$ may be hydrogen or oxo and $R^3$ and $R^4$, together, may represent $(CH)_2S$, or $R^2$ may be hydrogen and $R^3$ and $R^4$ may, together, represent $(CH_2)_4$, forming an octahydronaphthalene, or $R^2$ may be oxo and $R^3$ and $R^4$ may, together, represent $(CH_2)_4$, or $R^2$ may be oxo and $R^3$ and $R^4$, together, may represent $(CH)_2$ $C(CH_3)(CH)$, or $R^2$ may be hydrogen and $R^3$ and $R^4$, together, may represent $S(CH_2)_2$, or $R^2$, $R^3$ and $R^4$ may be H, or $R^2$ may be oxo and $R^3$ and $R^4$, together, may represent $(CH)_2$ $C(OCH_3)CH$, or $R^3$ and $R^4$ together may represent —$Y^1$—C $(R_2)_x$—$C(R_2)_x$—$Y^1$— wherein $Y^1$ is N, forming a tetrahydroquinoxaline wherein $R^2$ may be hydrogen or oxo.

Alternatively, in the compounds of Formula II

may represent a tetrahydroquinoline radical wherein $R^3$ and $R^4$ together are —$Y^1$—$C(R_2)_x$—$C(R_2)_x$—$C(R_2)_x$— wherein $Y^1$ is N. In such tetrahydroquinoline derivatives $(R^2)_x$ may be hydrogen or oxo; or may represent a tetrahydro-isoquinoline radical wherein $R^3$ and $R^4$ together are —$C(R_2)_x$—$Y^1$—$C(R_2)_x$—$C(R_2)_x$— wherein $Y^1$ is N and $(R^2)_x$ may be hydrogen or oxo.

Alternatively, in the compounds of Formula II

may represent a cyclopentyl radical.

In such cyclopentyl derivatives of Formula II, $R^2$ may be H and $R^3$ and $R^4$, together, may represent $(CH)_4$, or $R^2$ may be oxo and $R^3$ and $R^4$, together, may represent $(CH)_4$, or $R^2$ may be hydrogen and $R^3$ and $R^4$, together, may represent $(CH_2)_3$.

In another aspect of the invention, Y is $(CH_2)_3$ and X may be CH and $R^2$ may be oxo or X may be $CH_2$ and $R^2$ may be H and $R^3$ and $R^4$, together, may represent $(CH)_4$. Alternatively, $R^3$ and $R^4$, together, may represent $(CH)_4$, Y may be $CH_2C(CR^1_2)_2$ wherein $R^1$ is hydrogen, or Y may be —CH2C(Me)- and $R^2$ may be hydrogen or oxo.

Finally, in the compounds of Formula II

may represent a phenyl radical.

In such phenyl derivatives of Formula I, X may be $CH_2$, R maybe H or $CH_3$, $R^2$, $R^3$ and $R^4$ may be H, or $R^3$ and $R^4$, together, represent $O(CR^2)_2O$ to provide a 1,4-benzodioxan derivative.

In another aspect of the invention, said compound has the formula

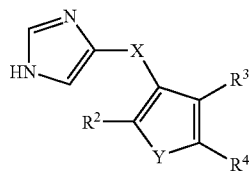

III wherein Y is S or O.

In such compound of Formula III, X may be $C(H)R^1$, $R^1$, $R^2$, $R^3$ and $R^4$ may be H and Y may be O or S.

In another aspect of the invention, said compound has the formula

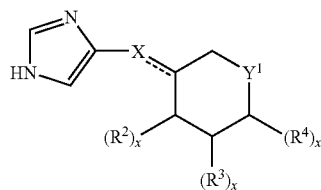

IV and $R^3$ and $R^4$, together, represent $(CH)_4$.

In such compounds of Formula IV, $Y^1$ may be O, $R^2$ may be oxo and X is CH or $CH_2$, or one of $R^2$ is hydroxy and the other may be H, or $R^2$ may be H.

In such compounds of Formula IV, $Y^1$ may be S, X may be $CH_2$ and $R^2$ may be oxo, or $R^2$ may be H and X may be CH and $R^2$ may be oxo.

To prepare the compounds of U.S. Pat. No. 6,329,369 the starting cyano compound has the formula

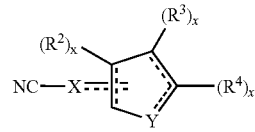

The following defined terms are used throughout this specification:

"Ac" refers to acetyl.
"Me" refers to methyl.
"Et" refers to ethyl.
"tBu" refers to t-butyl.
"iPr" refers to i-propyl.
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, CH$_2$CN, alkyaryl, sulfonamide, NH-alkyl, NH-alkylaryl, or NH-aryl.

As disclosed above, it is important that the cyano compound does not have a benzylic or allylic hydrogen at the position alpha to the cyano group.

Thus, the following cyano compounds are excluded from the method of the present invention.

wherein Ar is aryl; and

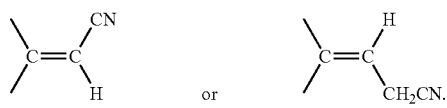

Specific examples of cyano compounds useful in the method of the present invention and the resulting imidizoles are as follows:

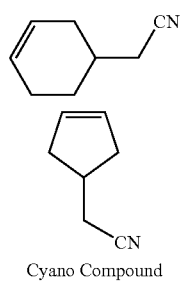

Cyano Compound

-continued

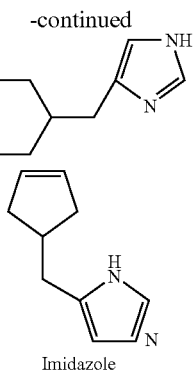

Imidazole

In the following examples, the numerals correspond to the numerals in the FIGURE.

The invention is further illustrated by the following examples which are illustrative of a specific mode of practicing the invention and is not intended as limiting the scope of the appended claims.

EXAMPLE 1

Trimethylsilylmethyl Formamide (3)

A 2 L three necked flask equipped with a mechanical stirrer, condenser with an argon inlet, and addition funnel was charged with dimethylformamide (450) mL) and sodium hydride (17.4 g, 0.72 mol). To this mixture, formamide (2) (21.1 g, 0.69 mol) dissolved in 50 ml of dimethylformamide was added dropwise over a period of 30 min. The reaction was then heated to 120° C. in an oil bath. The mixture changed from gray to brown over a period of 45 min. The resulting suspension was cooled to 60° C. and chloromethyltrimethylsilane (1) (84.6 g, 0.69 mol) was then added all at once. The reaction was heated to 120° C. and stirred overnight. The reaction was filtered and the filtrate distilled. The product was obtained at 130-140° C. @ 12 Torr to give 70.6 g of 3 (78%).

EXAMPLE 2

Trimethylsilylmethyl Isocyanide (4)

A 2 L three necked flask equipped with a mechanical stirrer, thermometer, and an addition funnel with an argon inlet was charged with trimethylsilylmethylformamide (3) (69.4 g, 0.53 mol), diisopropylamine (144.5 g, 1.43 mol), and dichloromethane (520 mL). The solution was cooled in a dry ice-acetone bath to an internal temperature of −20° C. To this solution phosphorus oxychloride (89.5 g, 0.583 mol) dissolved in 80 ml of dichloromethane was added at such a rate as to maintain the temperature around −20° C. The time for complete addition was approximately 75 min. The cooling bath was replaced with an ice water bath and the pink suspension was stirred at 0° C. for 1 hr. The reaction was then diluted with 1 L aqueous solution of 293 g of potassium carbonate cooled to 0° C. The cooling bath was removed and the resulting mixture was stirred an additional 1 hr. The layers were separated and the aqueous phase was extracted with 2×200 mL of dichloromethane. The organic phases were combined, washed with 2×250 ml of aqueous ammonium chloride, and dried over sodium sulfate. The solvent was removed on a rotary evaporator at 32° C. until the pressure dropped to 60 Torr. The resulting brown residue was distilled and the impure product was collected at 50° C. @ 0.2 Torr the receiving flask was cooled in a dry ice-acetone bath. The distillate was redistilled at 80-87° C. @ 90 Torr to give 33 g of product 4 (55%).

EXAMPLE 3

4(5)-(cyclohexene-4-ylmethyl) Imidazole (7)

Under an argon atmosphere potassium tert-butoxide (2.47 g, 0.02 mol) was added to 15 ml of dimethoxyethane. A brown suspension formed immediately. The flask was cooled in a room temperature water bath. To this mixture a solution of trimethylsilylmethyl isocyanide (3.39 g, 0.03 mol) and 3-cyclohexene-1-acetonitrile (2.42 g, 0.02 mol) in 5 mL of dimethoxyethane was added over period of 25 min. The reaction was stirred an additional 15 min. and HPLC analysis showed 71% imidazole (7) and 26% silylimidazole (6). After an additional 30 min. potassium fluoride (1 g, 0.017 mol) was added and the reaction was refluxed an additional 8 hr. The reaction was cooled to room temperature, diluted with 50 mL of brine, and extracted with 50 mL of ethyl acetate. The organic layer was washed with 50 mL of brine, filtered through 1 PS paper and the solvent was removed on a rotary evaporator to give 2.5 g of a brownish-red oil. Two identical reactions were combined and flash column chromatographed on 50 g of flash silica gel with 10 g of anhydrous sodium sulfate on top. The column was eluted with 100 ml portions of ethyl acetate for the first 4 fractions and 10% methanol in ethyl acetate for fraction 5-8. The product came off the column in fractions 5 and 6 to give 3.6 g of an oil upon removal of the solvent in vacuo. The oil crystallized upon tituration with hexanes to give 3.4 g of light brown solid that was 100% pure by HPLC analysis in overall yield of 52%.

HPLC: Column: Phenominex prodigy-5 micron, 250 mm; mobile phase; water: $A_1$ MeOH; 5:45:40 ($A_1$ is mode of 700 mL water, 300 mL methanol, 3 mL triethylamine with enough phosphoric acid to give pH 3.4). The retention time of the imidazole was 2.8 min. and the silylated imidazole showed a retention time of 6.2 min.

EXAMPLE 4

2-Cyclopent-3-enylethanenitrile (8)

In a 1 L three neck round bottom flask, a mixture of NaCN (51 g, 1.04 mol) in anh. DMSO (200 ml) was heated to 75-80° C. To this slurry was added, drop wise, a solution of 4 (218.16 g, 0.86 mol) in DMSO (300 ml) (the addition time was 45 min.). After the addition finished, the reaction mixture was left stirring at 80° C. for another 2 h. Completion of the reaction was monitored by NMR for the disappearance of cyclopent-3-enylmethyl-4-methylbenzenesulfonate. The reaction mixture was then cooled and diluted with water (200 ml) and extracted with hexane (5×250 ml). The combined organic layers were washed with brine (200 ml) and dried ($MgSO_4$). The solvent was then removed under vacuo to obtain the product 8 as a yellow oil in 91.58 g (99%). The crude product showed some impurities in ca. 10% (by $^1$H NMR integration) but was used in the next step without purification. $^1$H NMR (CDCl3) δ: 2.20 (m, 2H), 2.40 (m, 2H), 2.70 (m, 3H), 5.70 (s, 2H).

EXAMPLE 5

4-(Cyclopent-3-enylmethyl)imidazole (9)

In a 2 L three neck bottom flask, a mixture of t-BuOK (115 g, 1.02 mol) in anh. THF (500 ml) was cooled to −15° C. To this slurry was added a mixture of (91.58 g, 0.85 mol) and $TMSCH_2NC$ (144 ml, 1.02 mol) in anh. THF (400 ml) via an addition funnel at a rate such that the temperature was maintained at 0.15° C. The cooling bath was removed and the reaction mixture was left stirring for 2.5 h. The completion of reaction was monitored by TLC (5% MeOH in $CH_2Cl_2$) for the disappearance of 8. The reaction mixture was then worked up by washing with water (400 ml). The aqueous layer was extracted again with $CH_2Cl_2$ (2×250 ml). The combined organic layers were washed with brine (300 ml) and dried ($MgSO_4$). After the solvent was removed, a mixture of products was obtained as a dark brown oil. To the crude reaction mixture was added with a solution of TBAF-$xH_2O$ (100 g, 0.38 mol) in THF (400 ml) and 12M TBAF in THF (100 ml, 0.1 mol). The reaction mixture was then stirred at 70° C. for 16 h. The completion of the desilylation was monitored by $^1$H NMR. The solvent was removed from the reaction mixture under vacuo. The residue was then dissolved with acetone (300 ml) and was treated with a solution of oxalic acid (78 g, 0.87 mol) in acetone (300 ml). The mixture was stirred for 15 min. at room temperature. The resulting solid was collected by filtration and was rinsed with acetone (2×20 ml) to obtain a light brown solid including an oxalate salt in 112 g (55%). $^1$H NMR (d6-DMSO) δ: 2.05 (m, 2H), 2.40 (m, 2H), 2.50-2.75 (m, 3H), 5.70 (s, 2H), 7.15 (s, 1H), 8.35 (s, 1H).

The oxalate salt was liberated by dissolving in 2N NaOH (500 ml) and extracted with $CH_2Cl_2$ (3×250 ml). The combined organic layers were dried ($MgSO_4$) and the solvent was removed under vacuo to obtain a brown oil, which solidified upon standing at room temperature, in 67.94 g (53% from 8). $^1$H NMR (CDCl$_3$) δ: 2.10 (m, 2H), 2.50 (m, 2H), 2.75 (m, 3H), 5.70 (s,2H), 6.80 (s, 1H), 7.70 (s, 1H).

EXAMPLE 6

In accordance with the procedure of Example 3, isobutyronitrile is reacted with trimethylsilymethylisocyanide to yield 4(5)-isopropylimidazole.

EXAMPLE 7

In accordance with the procedure of Example 3, benzonitrile is reacted with trimethylsilymethyl isocyanide to yield 4(5)-phenylimidazole.

EXAMPLE 8

In accordance with the procedure of Example 3, trimethylacetonitrile is reacted with trimethylsilylmethyl isocyanide to yield 4(5)-t-butylimidazole.

EXAMPLE 9

In accordance with the procedure of Example 3, α, α-dimethylbenzylcyanide is reacted with trimethylsilylmethyl isocyanide to yield 4(5)-α, α-dimethylbenzylimidazole.

EXAMPLE 10

In accordance with the procedure of Example 3, 3-cyanopyridine is reacted with trimethylsilylmethyl isocyanide to yield 4(5)-(3-pyridyl)imidazole.

EXAMPLE 11

In accordance with the procedure of Example 3, thiophene-2-carbonitrile is reacted with trimthylsilylmethyl isocyanide to yield 4(5)-(2-thienyl)imidazole.

EXAMPLE 12

In accordance with the procedure of Example 3, thiophene-3-carbonitrile is reacted with trimethylsilylmethyl isocyanide to yield 4(5)-(3-thienyl)imidazole.

EXAMPLE 13

In accordance with the procedure of Example 3, 3-phenyl-propionitrile is reacted with trimethylsilylmethyl isocyanide to yield 4(5)-(2-phenethyl)imidazole.

While particular embodiments of the invention have been described, it will be understood of course that many obvious modifications can be made and it is intended to include within this invention any such modifications as will fall within the scope of the appended claims.

For example, instead of trimethylsilymethyl isocyanide trimethyl(lower alkyl)methyl isocyanide may be used in any of the above examples to provide imidazoles of the formula

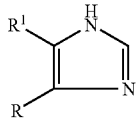

The invention claimed is:

1. A compound of the formula

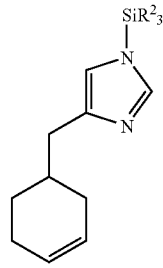

wherein each $R^2$ is independently H or alkyl having from 1 to 6 carbon atoms.

2. The compound of claim 1 of the formula

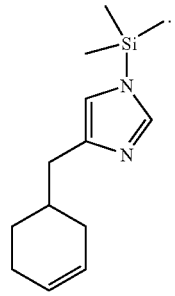

* * * * *